(12) United States Patent
Gupta et al.

(10) Patent No.: US 9,475,780 B2
(45) Date of Patent: Oct. 25, 2016

(54) PROCESS FOR THE SYNTHESIS OF CYCLIC ALKYLENE UREAS

(75) Inventors: Ram Gupta, Stamford, CT (US); Irina Kobylanska, Stamford, CT (US); Urvee Treasurer, Stamford, CT (US); Lawrence Flood, Norwalk, CT (US)

(73) Assignee: Allnex IP S.ar.L., Luxembourg (LU)

(*) Notice: Subject to any disclaimer, the term of this patent is extended or adjusted under 35 U.S.C. 154(b) by 74 days.

(21) Appl. No.: 14/233,302

(22) PCT Filed: Jul. 19, 2012

(86) PCT No.: PCT/US2012/047305
§ 371 (c)(1),
(2), (4) Date: Jan. 16, 2014

(87) PCT Pub. No.: WO2013/012991
PCT Pub. Date: Jan. 24, 2013

(65) Prior Publication Data
US 2014/0163221 A1 Jun. 12, 2014

(30) Foreign Application Priority Data
Jul. 20, 2011 (EP) .................................... 11174656

(51) Int. Cl.
*C07C 275/00* (2006.01)
*C07D 243/04* (2006.01)
*C07D 233/34* (2006.01)
*C07D 239/10* (2006.01)

(52) U.S. Cl.
CPC ........... *C07D 243/04* (2013.01); *C07D 233/34* (2013.01); *C07D 239/10* (2013.01)

(58) Field of Classification Search
None
See application file for complete search history.

(56) References Cited

U.S. PATENT DOCUMENTS

| 2,436,311 | A |   | 2/1948  | Larson et al. |
| 2,504,431 | A |   | 4/1950  | Loder |
| 2,526,757 | A |   | 10/1950 | Larson et al. |
| 2,892,843 | A |   | 6/1959  | Levine |
| 5,902,899 | A | * | 5/1999  | Hayashi ............ C07C 273/1809 546/306 |
| 2010/0113819 | A1 |  | 5/2010  | Belfadhel et al. |
| 2010/0261015 | A1 |  | 10/2010 | Szafranski et al. |

FOREIGN PATENT DOCUMENTS

JP    H10-251214 A    9/1998

OTHER PUBLICATIONS

International Search Report for PCT/US2012/047305 mailed Sep. 11, 2012.
Ballini, R., et al., "TBD—Catalysed Solventless Synthesis of Symmetrically N,N'-Substituted Ureas from Primary Amines and Diethyl Carbonate", Green Chemistry, (2003), vol. 5, pp. 396-398.
Han, C., et al., "Synthesis of Carbamates and Ureas Using Zr(IV)-Catalyzed Exchange Processes", Organic Letters, (2007), vol. 9, No. 8, pp. 1517-1520.
Bachmann et al., "The Nitration of Derivatives of Ethylenediamine", Journal of the American Chemical Society, 1950, vol. 72, pp. 3132-3134.
Jagtap et al., "Heterogeneous Base Catalyzed Synthesis of 2-Oxazolidinones/2-Imidazolidinones via Transesterification of Ethylene Carbonate with β-aminoalcohols/ 1,2-diamines", Applied Catalysis A: General, 2008, vol. 341, pp. 133-138.
Xiao et al., "A Method for the Synthesis of 2-oxazolidinones and 2-imidazolidinones rom five-membered cyclic carbonates and β-aminoalcohols or 1,2-diamines", Green Chemistry, 2007, vol. 9, pp. 369-372.
Schweitzer, "Ethyleneurea I. Synthesis from Urea and Ethylenediamine", Org. Chem., 1950, vol. 15, pp. 471-474.
Schweitzer, "Ethyleneurea. II. Synthesis from Ethylene Glycol or Ethanolamine and Urea (or Carbon Dioxide and Ammonia)", Org. Chem, vol. 15, pp. 475-480, 1949.
Fischer et al., "Ueber einige Derivates des Trimethylen- und Aethylendiamins", Annalen, 1886, vol. 232, pp. 227.

* cited by examiner

*Primary Examiner* — Clinton Brooks
*Assistant Examiner* — Jennifer C Sawyer
(74) *Attorney, Agent, or Firm* — Drinker Biddle & Reath LLP

(57) ABSTRACT

The invention relates to a process for the synthesis of cyclic alkylene ureas comprising reacting in the presence of a basic catalyst, a difunctional amine A having two primary amino groups, and an aliphatic organic carbonate component C selected from the group consisting of dialkyl carbonates CD and of alkylene carbonates CA, wherein the ratio of the amount of substance Ji(—NH2) of primary amino groups —NH2 in the difunctional amine A to the sum M(C) of the amount of substance n(CD) of carbonate groups of a dialkyl carbonate CD and the amount of substance n(CA) of carbonate groups in an alkylene carbonate CA, is at least more than 2, and to the product obtained by this process.

18 Claims, No Drawings

PROCESS FOR THE SYNTHESIS OF CYCLIC ALKYLENE UREAS

CROSS-REFERENCE TO RELATED APPLICATIONS

This application is a national stage application (under 35 U.S.C. §371) of PCT/US2012/047305, filed Jul. 19, 2012, which claims benefit of European application 11174656.6, filed Jul. 20, 2011.

FIELD OF THE INVENTION

The invention relates to a process for the synthesis of cyclic alkylene ureas, and to the products obtained from this process.

BACKGROUND OF THE INVENTION

Various processes to make cyclic alkylene ureas have been described in the literature and in patents, such as in J. Org. Chem. 1950, vol. 15, pages 471 to 474, and 475 to 480, relating to the synthesis of ethylene urea from urea and ethylenediamine, and from ethylene glycol or ethanolamine and urea, or carbon dioxide and ammonia.

As early as 1886, E. Fischer and H. Koch reported in Annalen, vol. 232, page 227 (1886), the preparation of ethylene urea by heating ethylenediamine and diethyl carbonate at 180° C. As described therein, this reaction was carried out in a sealed tube and required the use of high temperature.

In U.S. Pat. Nos. 2,436,311, 2,504,431, 2,526,757, as well as in the patent publication US 2010/0261015 A1, a process is disclosed for the manufacture of ethylene urea by the reaction of 1,2-ethylenediamine with urea, wherein these two starting materials are mixed and heated to a temperature of at least from 240° C. to 260° C. As described in these patents, this reaction appears to proceed through a series of stages at temperature between 100° C. and 260° C. at atmospheric or elevated pressure. Release of ammonia, a by-product of this reaction, begins as the reaction mixture reaches 100° C. to 115° C. This reaction is carried to completion by continued heating usually to an end temperature of from 170° C. to 240° C. According to these prior art references the reaction can be carried out under anhydrous conditions or in presence of water and/or a high boiling solvent such as ethylene glycol and diethylene glycol, however, the beneficial use of water in markedly increasing the yield versus reactions conducted under anhydrous conditions is noted and exemplified. Water is believed to be responsible for the more complete conversion of the intermediate condensation product to ethylene urea. The crude ethylene urea thus formed does not form a clear solution in water but results in turbid solutions which are distinctly alkaline, while pure ethylene urea is fully soluble in water. The desired product ethylene urea is generally isolated from the aqueous solution by crystallisation as hemihydrate, and comprises a mass fraction from about 5% to 15% of water. Some of the disadvantages of this process route using urea as a reactant are the formation of water-insoluble by-products, the need to react at higher temperature and higher pressure conditions, and formation of hydrated ethylene urea which is not a free-flowing powder, but has a propensity to cake and form lumps.

Other processes using organic carbonates as a reactant include the previously disclosed reaction (U.S. Pat. No. 2,892,843) of cyclic 1,2-alkylene carbonates, namely ethylene carbonate or propylene carbonate, with ammonia at temperatures of from 200° C. to 290° C., and autogenous pressure.

A recent journal article in Applied Catalysis A: General 341 (2008), pages 133 to 138, describes the synthesis of 2-imidazolidinones via the trans-esterification of equal amounts of substance of ethylene carbonate and a diaminoalkane using a heterogeneous basic metal oxide catalyst like magnesium oxide, MgO.

SUMMARY OF THE INVENTION

It has been found in the experiments underlying the present invention that reaction of a difunctional primary aliphatic amine and an organic carbonate component which may be a dialkyl carbonate or an alkylene carbonate, in the presence of a basic catalyst, leads to formation of cyclic alkylene ureas in a good yield when the difunctional aliphatic amine is used in stoichiometric excess.

The object of the invention is therefore a process for the synthesis of cyclic alkylene ureas by reacting a difunctional aliphatic amine A having two primary amino groups, and an aliphatic organic carbonate component C selected from the group consisting of dialkyl carbonates CD and of alkylene carbonates CA, wherein the ratio of the amount of substance $n(-NH_2)$ of primary amino groups $-NH_2$ in the difunctional amine A to the sum $n(C)$ of the amount of substance $n(CD)$ of carbonate groups of the dialkyl carbonate CD and the amount of substance $n(CA)$ of carbonate groups of the alkylene carbonate CA, is at least more than 2.

This reaction is conducted in the presence of a basic catalyst which is preferably selected from the group consisting of alkoxides of alkali metals of group 1 of the Periodical System of Elements, and of alkoxides of earth alkali metals, of group 2 of the Periodical System of Elements, according to recent IUPAC nomenclature, and of mixtures thereof.

A primary difunctional amine, in the context of this invention, has exactly two primary amino groups.

DETAILED DESCRIPTION OF THE PREFERRED EMBODIMENTS

The preferred difunctional amines A have two primary amino groups attached to a linear or branched or cyclic aliphatic structure which preferably has from two to twenty carbon atoms. The two amino groups in the same molecule of a difunctional amine A are separated from each other by at least two successive carbon atoms. One or more of the carbon atoms may be separated by an oxygen atom in an ether bond, —C—O—C—, where any two oxygen atoms are preferably separated by two carbon atoms, forming a structure —C—O—C—C—O—C—. One or more of such oxygen atoms may be replaced by a sulphur atom. Preferred diprimary diamines A are ethylenediamine, 1,2-diaminopropane, 1,3-diaminopropane, 1,4-diaminobutane, 2,3-diaminobutane, 1,5-diaminopentane, 1,2-diaminocyclohexane, 1,6-diaminohexane, bis-(2-aminoethyl) ether, 1,12-diamino-4,9-dioxadodecane, and a mixture of 2,2,4- and 2,4,4-trimethyl-1,6-diaminohexane. Particularly preferred difunctional amines are 1,2-diaminoethane, 1,2- and 1,3-diaminopropane, 1,4- and 2,3-diaminobutane, as well as mixtures of these.

In a further embodiment, the amine A is has the structure

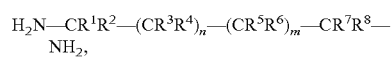

where any of the radicals $R^i$ with i ranging from 1 to 8 may independently from any other of the said radicals be H, an alkyl group having from one to eight carbon atoms and being linear branched or cyclic, an alkenyl group having at least one olefinic unsaturation and from one to eight carbon atoms and being linear branched or cyclic, an alkoxy group having from one to eight carbon atoms and being linear branched or cyclic, or a carboxyl or carboxyl ester group, and n and m may independently be 0 or 1. One or more of $R^3$, $R^4$, $R^5$, and $R^6$ may also be a halogen atom, or a hydroxyl group. In the case of n and m being zero, a C-substituted ethylene urea is the reaction product, e.g., a 4,4-dialkyl ethylene urea or a 4,5-dialkyl ethylene urea, a 4-vinyl ethylene urea or a 4-methoxy ethylene urea. In of the case of n being 1, and m being zero, or n being zero and m being 1, a C-substituted propylene urea is obtained such as, e.g., 4-methyl propylene urea, 5-halogen propylene urea, 5-hydroxy propylene urea, 5,5-dimethylpropylene urea, 5-carboxypropylene urea, the ethyl ester of propylene urea-5-carboxylic acid, and 5-methoxy propylene urea. If both m and n are 1, a C-substituted butylene urea is obtained such as 5-hydroxybutylene urea, 5,6-dihydroxybutylene urea, 4-alkyl butylene urea, 4,5,6,7-tetraalkyl butylene urea, and 4,7-dimethylbutylene urea.

The aliphatic organic carbonate component, C, can be an alkylene carbonate CA, or a dialkyl carbonate, CD, or a mixture of these.

Alkylene carbonates CA are cyclic esters of dihydroxyalkanes preferably having from two to six carbon atoms, such as ethylenecarbonate, 1,2- and 1,3-propylenecarbonate. Useful alkylene carbonates are ethylenecarbonate and 1,2-propylenecarbonate, which are both commercially available.

Dialkyl carbonates CD have the structure $R^a$—O—CO—O—$R^b$, where $R^a$ and $R^b$ may be the same, or may be different, and may independently be selected from the group consisting of linear and branched alkyl radicals having from one to twelve carbon atoms. Especially preferred are dimethyl carbonate, and diethyl carbonate, and mixtures of these.

Basic catalysts which have proved to be useful for the invention are preferably alkali metal or earth alkali metal alkoxides, particularly preferred, lithium methoxide, sodium methoxide and potassium methoxide, or the ethoxides of lithium, sodium, and potassium, and mixtures of these. In a further embodiment, alkali alkoxides or earth alkali alkoxides may be generated in situ, such as from an alkanol and an alkali or earth alkali hydroxide, preferably under removal of water, or by reaction of an alkali or earth alkali metal, their amides, or their hydrides, with an alkanol.

Although it would have been expected by a person skilled in the art that the best yield of the desired cyclic urea would be achieved by using stoichiometric amounts of the amine component and the carbonate component, as the formation of linear oligomers would be favoured when using a stoichiometric excess of one of the reactants, it has unexpectedly been discovered that using the aliphatic amine in a quantity exceeding the stoichiometric quantity has significant advantages such as on yield and purity.

The ratio $n(-NH_2)/n(C)$ of the amount of substance $n(-NH_2)$ of primary amino groups $-NH_2$ in the aliphatic amine A to the sum n(C) of the amount of substance n(CD) of carbonate groups of dialkyl carbonate CD and the amount of substance n(CA) of carbonate groups in alkylene carbonate CA present in the carbonate component, C, is at least more than 2, in accordance with the invention:

$$n(-NH_2)/n(C)=n(-NH_2)/[n(CD)+n(CA)]>2.$$

Preferably, this ratio $n(-NH_2)/n(C)$ is at least 2.2, particularly preferably, at least 2.4, and with special preference, at least 2.5. Good results have also been obtained when the ratio is at least three, or with more preference, at least four.

When a diprimary diamine such as ethylenediamine or 1,3-diaminopropane is used in the reaction with a carbonate compound, a cyclic urea having two amidic N—H groups is formed, in this case, ethyleneurea or propyleneurea.

The process according to the invention preferably comprises the following steps:

charging both the difunctional amine A and the carbonate C to a reaction vessel, optionally adding a solvent which is selected from the group consisting of aliphatic linear, branched or cyclic alcohols having from one to eighteen carbon atoms, aliphatic diols having a linear or branched alkylene chain of from two to six carbon atoms, monoalkyl ethers of any of the said alcohols where the alkyl groups have from one to four carbon atoms, monoalkyl ethers or dialkyl ethers of any of the said glycols where the alkyl groups have independently from one to four carbon atoms, and of alkyl aromatic compounds, and of mixtures of two or more of any of these, holding the mixture at a temperature of from 0° C. to 250° C., adding the basic catalyst, preferably under stirring, further holding the reaction mixture at a temperature of from 25° C. to 250° C. during the reaction, and isolation of the cyclic alkylene urea formed.

In a further preferred embodiment, a mixture of solvent, difunctional amine A, and preferably, also catalyst is charged into a reactor, and the carbonate component C is added preferably over a time span of between fifteen minutes and six hours, under mixing conditions such as stirring, or circulating the reaction mixture in a tubular loop which includes at least one mixing section which may be a nozzle set into a tube, or a static mixer. Another process that can be used comprises therefore the following steps:

charging both the difunctional amine A and the basic catalyst to a reaction vessel, optionally adding a solvent which is selected from the group consisting of aliphatic linear, branched or cyclic alcohols having from one to eighteen carbon atoms, aliphatic glycols having a linear or branched alkylene chain of from two to six carbon atoms, monoalkyl ethers of any of the preceding alcohols where the alkyl groups have from one to four carbon atoms, monoalkyl ethers or dialkyl ethers of any of the preceding glycols where the alkyl groups have independently from one to four carbon atoms, and of alkyl aromatic compounds, and of mixtures of two or more of any of these, holding the mixture at a temperature of from 0° C. to 250° C., adding the carbonate component C under stirring, further holding the reaction mixture at a temperature of from 25° C. to 250° C. during the reaction, and isolation of the cyclic alkylene urea formed.

The difunctional amine A, the carbonate C, and the catalyst, may be charged in any order to a reaction vessel. If a solvent is used, it may be charged before addition of the reactants and catalyst, or may be added together with any of these, or may be added last. It is preferred to at least partially replace the air by nitrogen or an other inert gas. The reaction mixture is preferably heated, and continued until the reaction is essentially complete, as evidenced by samples drawn from the reaction mixture. The alcohol released from the carbonate component C, and excess amine A may then be removed, preferably by distillation under reduced pressure. The cyclic alkylene urea formed is then isolated.

If a solvent is used, and the cyclic alkylene urea is not soluble in the solvent used, the reaction product is preferably isolated as a precipitate by filtration, before or after removal of the excess amine, and the alcohol is preferably removed by distillation under reduced pressure. The precipitate may then be washed with further solvent. If a solvent is used, and the cyclic alkylene urea is significantly soluble in the solvent, the cyclic alkylene urea may be recovered by partially or completely removing the solvent, or it may be precipitated from the solution by adding a non-solvent, or a combination of both processes.

A substance is called "not soluble" in a specified solvent if it is not significantly soluble in this solvent, at ambient temperature (20° C.). By "not significantly soluble" it is meant that the mass fraction of the substance in question dissolved in a solvent which is in equilibrium with the substance in question is preferably not more than 10%.

If no solvent is used, the remaining solids after removing the excess amine and the alcohol by distillation under reduced pressure are washed with one or more of the solvents mentioned.

The washed precipitate usually has a purity of more than 90%. For further purification, further washing steps, recrystallisation, melt crystallisation, or dissolution of the cyclic alkylene urea in water to form a solution which may be purified by ion exchange or adsorption methods can be preferably used. Residual unreacted difunctional amine can be removed by treatment with ion exchange resins.

The most preferred process is conducted by charging the amine A, the carbonate component C, and the catalyst to a reaction vessel, optionally adding a solvent as detailed infra, optionally, at least partially replacing the air by nitrogen or an other inert gas, and holding the mixture at a reaction temperature of between 0° C. to 250° C. The upper temperature limit is preferably chosen to allow reflux, or support fractional distillation to separate the cyclic urea from reaction byproducts.

The basic catalyst can be added together with the reactants, or preferably, is slowly added to the mixture of reactants as charged, or to the pre-heated reactants, preferably during a period of between ten minutes and sixty minutes, under stirring. Heating and stirring the reaction mixture is then continued until the reaction has proceeded to essential completion, as shown by the amount of alcohol or diol formed from the carbonate component, C, then separating the excess amine A and alcohol or diol released from the carbonate component C by distillation under reduced pressure, filtering of the residue, and isolating of the cyclic alkylene urea formed.

In a variant, a solvent can be added to the reactants, which solvent is selected from the group consisting of aliphatic linear, branched or cyclic alcohols having from one to eighteen carbon atoms, such as n-butanol or isopropanol, aliphatic glycols having a linear or branched alkylene chain of from two to six carbon atoms, such as ethylene glycol or 1,2-propylene glycol, monoalkyl ethers of any of the alcohols, where the alkyl groups have from one to four carbon atoms, monoalkyl ethers or dialkyl ethers of any of the preceding where the alkyl groups independently have from one to four carbon atoms, such as methoxypropanol, ethoxybutanol, or 1,4-dimethoxybutane, and of alkyl aromatic compounds or mixtures thereof, such as toluene, xylene, ethyl benzene, and methyl naphthalene, and of mixtures of two or more of any of these. The solvent is chosen to be inert under the reaction conditions, i.e., so that is does not react with any of the starting materials, or with the desired end product.

In one approach, the excess difunctional amine A and the alcohol formed in the reaction is removed by, e.g., distillation under reduced pressure. Upon cooling, the alkylene urea usually solidifies, or separates from the solvent if a solvent is present. Such solvent is chosen to dissolve the alkylene urea only slightly or not at all. It is also possible to separate the cyclic alkylene urea from the unreacted amine and the alcohol formed, by filtration from the reaction mixture after cooling if it forms a solid. Aliphatic ethers like dimethoxyethane or alkyl aromatic compounds such as toluene or xylene or mixtures of these optionally with mesitylene and cumene which are sold as "solvent naphtha" are particularly suitable. Isolation is then best effected by filtration, in the case of solid products, which leaves the solid alkylene urea which is at most only sparingly soluble in the said solvents. Ketones which cannot be used during the reaction as solvents, like acetone and methyl isobutyl ketone, have been found useful when washing the isolated cyclic alkylene urea.

An important advantage of the process claimed is the essential absence of water in the reaction which leads to the low level of water in the final product. In the case where the cyclic urea is solid at ambient temperature (20° C.), such as ethylene urea and propylene urea, this process allows to obtain the cyclic urea as a free-flowing solid, and also, in the form of free-flowing prills, with little or no propensity to form aggregates. The mass fraction of water in the final product is not more than 5%, and is preferably found to be not more than 1%.

The invention is further illustrated by the following examples which are not intended to be limiting.

The following analytical tools were used:

$^{13}$C-NMR: Samples were dissolved in $D_2O$ for analysis as solutions having a mass fraction of solute of 10%. The NMR spectra were acquired on a Bruker Avance II 400 NMR spectrometer using a 10 mm PABBO probe with the "quant2_45" method with the D1 delay increased from 10 s to 30 s to give better quantitation for the carbonyl peaks.

GC/MS Conditions: samples were dissolved in acetonitrile to make solutions having a mass fraction of solute of 0.5%. The injection port temperature was 225° C., the column temperature was initially 175° C., rising by 20 K/min until 200° C. was reached. A constant helium flow of 1 mL/min was used.

FTIR: Infrared spectra were acquired using a DuraScope single reflection diamond ATR accessory mounted in the sample chamber of a Digilab 7000e FTIR spectrometer.

EXAMPLES

In these examples, and also in the remaining specification, the following definitions apply:

"Purity" is the ratio of the mass of the desired product to the mass of the material used (when used as starting material) or obtained (when present in the reaction product), usually measured in "%", or cg/g.

"Strength" is the mass fraction $w_B$ of solute B in a solution S, calculated as the ratio of the mass $m_B$ of solute B and the mass $m_S$ of the solution, usually measured in "%", or cg/g.

Yield is the ratio of the mass of the desired reaction product obtained in a chemical reaction or a physicochemical process, and the expected mass of the reaction product without any loss due to side reactions or lost product during isolation thereof.

Example 1

A product was prepared by the following procedure according to the invention:

120.6 g (2 mol) of ethylenediamine (having a purity of 99.5%) and 45.45 g (0.5 mol) of dimethyl carbonate (having a purity of 99%) were charged to a reaction vessel under a nitrogen purge and mixed at room temperature (23° C.). 10.8 g (0.05 mol) of a 25% strength solution of sodium methoxide in methanol was slowly added into reaction mixture under mixing. An exotherm was observed and temperature increase to 60° C. in the absence of external cooling was recorded. After one hour of mixing, the temperature was gradually increased to 115° C. and held for one hour. During this period a distillate stream was collected. A white precipitate was formed upon cooling of the reaction mixture. The reaction mixture was concentrated by distillation under reduced pressure (25 kPa) at 95° C. to remove methanol and other volatile materials, and the precipitate was washed with acetone. The resulting product was analysed by $^{13}$C-NMR and found to be ethylene urea with a purity of 94% and a yield of 80%. The isolated product had a mass fraction of water of less than 1% as determined by Karl Fischer-titration, and a mass fraction of residual ethylenediamine of 250 mg/kg, as determined by GC-MS.

Example 2

A product was prepared by the following procedure according to the invention:

96.48 g (1.6 mol) of ethylenediamine (having a purity of 99.5%), 36.36 g (0.4 mol) of a dimethyl carbonate (having a purity of 99%) and 25.05 g (0.4 mol) of ethylene glycol were charged to a reaction vessel under a nitrogen purge and mixed at room temperature (23° C.). An exotherm was observed and temperature increase to 63° C. was recorded. After one hour, 7.2 g (0.04 mol) of a 30% strength solution of sodium methoxide in methanol was slowly added to the reaction mixture under stirring, and the temperature was gradually increased to 95° C. and held for two hours. A white precipitate was formed upon cooling of the reaction mixture. The reaction mixture was concentrated by distillation under reduced pressure (25 kPa) at 95° C. to remove methanol and other volatile materials, and the precipitate was washed with acetone. The isolated product was analysed by $^{13}$C-NMR and found to be ethylene urea, with a purity of 89%, in a yield of 81%.

Example 3

A product was prepared by the following procedure according to the invention:

96.48 g (1.6 mol) of an ethylenediamine (having a purity of 99.5%), 36.36 g (0.4 mol) of a dimethyl carbonate (having a purity of 99%) and 36.36 g (0.4 mol) of ethylene glycol diethyl ether were charged to a reaction vessel under a nitrogen purge and mixed at room temperature (23° C.). An exotherm was observed, and temperature increase to 55° C. was recorded. After one hour, 7.2 g (0.04 mol) of a 30% strength solution of sodium methoxide in methanol was slowly added to reaction mixture under stirring, and the temperature was gradually raised to 95° C. and held for two hour, then to 110° C., and distillate was collected. A white precipitate was formed upon cooling the reaction mixture. The reaction mixture was concentrated by distillation under reduced pressure (25 kPa) at 95° C. to remove methanol and other volatile materials, and the precipitate was washed with acetone. The isolated product was analysed by infrared spectroscopy and found to be ethylene urea in a yield of 80%, having a mass fraction of water of less than 1%.

Example 4

A product was prepared by the following procedure according to the invention:

120.6 g (2 mol) of ethylenediamine (having a purity of 99.5%), 45.5 g (0.5 mol) of dimethyl carbonate (having a purity of 99%) and 46.5 g (0.5 mol) of toluene and 10.8 g (0.05 mol) of a 25% strength solution of sodium methoxide in methanol were charged to a reaction vessel under nitrogen purge and mixed at room temperature. An exotherm was observed and a temperature increase to 56° C. was recorded. After one hour, the temperature was gradually increased to 95° C. and held for two hours, then to 110° C., and distillate was collected, then the temperature was further increased to 120° C. and held for two hours. A white precipitate was formed upon cooling of the reaction mixture. The reaction mixture was concentrated by distillation under reduced pressure (25 kPa) at 95° C. to remove methanol and other volatile materials, and the precipitate was washed with acetone.

The isolated product was analysed by $^{13}$C-NMR spectroscopy, and found to be ethylene urea. Its melting temperature was 135° C., and the mass fraction of water was found to be 0.4% by Karl Fischer-titration. The yield was 90%.

Example 5

A product according to the invention was prepared by the following procedure:

60.3 g (1 mol) of ethylenediamine (having a purity of 99.5%), 45.45 g (0.5 mol) of dimethyl carbonate (having a purity of 99%), 92.93 g (1 mol) of toluene, and 4.5 g (0.025 mol) of a 30% strength solution of sodium methoxide in methanol were charged to a reaction vessel under a nitrogen purge and mixed at room temperature. An exotherm was observed and temperature increase to 53° C. was recorded. After one hour the temperature was increased to 90° C. and distillate was collected, then temperature was gradually increased to 120° C., held for two hours during which distillate was collected. A white solid was formed upon cooling of the reaction mixture. The product was washed with toluene. The isolated product was analysed by $^{13}$C-NMR and found to be ethylene urea.

Example 6

A product according to the invention was prepared by the following procedure:

60.3 g (1 mol) of ethylenediamine (having a purity of 99.5%), 45.45 g (0.5 mol) of dimethyl carbonate (having a purity of 99%), 92.93 g (1 mol) of toluene, and 4.5 g (0.025 mol) of a 30% strength solution of sodium methoxide in methanol were charged to a reaction vessel under nitrogen purge and mixed at room temperature (23° C.). An exotherm was observed and temperature increase to 55° C. was recorded. After one hour, the temperature was increased to 90° C. and held for two hours at reflux. A white solid was formed upon cooling of the reaction mixture. The product was filtered and washed with toluene. The isolated product was analysed by $^{13}$C-NMR and found to be ethylene urea with purity of 97%, with a mass fraction of water of 0.4% as measured by Karl Fischer-titration. The mass fraction of residual ethylenediamine was found to be 150 mg/kg. The melting temperature of the ethylene urea formed was 135° C. The yield was 90%. Upon additional washing of this product with acetone, a product having a purity of 99.9% and a mass fraction of residual ethylenediamine of 100 mg/kg was obtained. The product was a free-flowing solid.

Example 7

A product according to the invention was prepared by the following procedure:

120.6 g (2 mol) of ethylenediamine (having a purity of 99.5%), 90.91 g (1 mol) of dimethyl carbonate (having a purity of 99%), 9.0 g (0.05 mol) of of a 30% strength solution of sodium methoxide in methanol were charged to a reaction vessel under a nitrogen purge and mixed at room temperature. An exotherm was observed and temperature increase to 60° C. was recorded. After one hour, the temperature was gradually increased to 95° C. and held for two hours, then to 110° C. and distillate was collected, then the temperature was increased to 120° C. and held for two hours. A white precipitate was formed upon cooling of the reaction mixture. The product was filtered and washed with acetone.

The isolated product was analysed by $^{13}$C-NMR and found to be ethylene urea with purity in excess of 97%.

Example 8

A product was prepared by the following procedure according to the invention:

72.36 g (1.2 mol) of ethylenediamine (having a purity of 99.5%), 36.36 g (0.4 mol) of dimethyl carbonate (having a purity of 99%) and 42.83 g (0.4 mol) of xylene were charged to a reaction vessel under a nitrogen purge and mixed at room temperature. No exotherm was observed and after one hour at room temperature (23° C.), 4.32 g (0.02 mol) of a 30% strength solution of sodium methoxide in methanol were slowly added. An exotherm was observed and a temperature increase to 65° C. was recorded. After one hour, the temperature was gradually increased to 95° C. and held for two hours, then raised to 110° C. At 97.5° C., the reaction mixture started to reflux, the mixture was then held for two hours under reflux and then, a white precipitate was formed upon cooling of the reaction mixture. The reaction mixture was concentrated by distillation under reduced pressure (25 kPa) at 95° C. to remove methanol and other volatile materials, and the precipitate was washed with methyl isobutyl ketone. The isolated product was analysed by GC/MS and found to be ethylene urea.

Example 9

A product was prepared by the following procedure according to the invention:

120.6 g (2 mol) of ethylenediamine (having a purity of 99.5%) and 44.44 g (0.5 mol) of ethylene carbonate (having a purity of 99%) were charged to a reaction vessel under a nitrogen purge and mixed at room temperature. No exotherm was observed. After one hour, 10.8 g (0.05 mol) of a 25% strength solution of sodium methoxide in methanol were slowly added to the reaction mixture under stirring and the temperature was gradually increased to 95° C. and held for two hours. A white slush was formed upon cooling of the reaction mixture. The reaction mixture was concentrated by distillation under reduced pressure (25 kPa) at 95° C., the product was separated by filtration and washed with acetone.

The isolated product was analysed by $^{13}$C-NMR, and found to be ethylene urea with presence of residual ethylene glycol.

Example 10

Comparative 241.2 g (4 mol) of ethylenediamine (having a purity of 99.5%) and 90.91 g (1 mol) of dimethyl carbonate (having a purity of 99%) were charged to a reaction vessel under a nitrogen purge and mixed at room temperature (23° C.). After one hour of mixing, the temperature was gradually increased to 115° C. and held for one hour. During this period, a distillate stream was collected. There was no precipitation formed upon cooling of the reaction mixture. The reaction mixture was concentrated under reduced pressure (25 kPa) at 95° C., and the precipitate was washed with acetone. The product was analysed by infrared spectroscopy and found to comprise only an insignificant amount of ethylene urea. This product exhibited a melting temperature in excess of 200° C., and unlike the product of Example 1, was only partially soluble in water, while ethylene urea is readily soluble in water.

Example 11

Comparative

A product was prepared by the following procedure:

30.15 g (0.5 mol) of ethylenediamine (having a purity of 99.5%) and 90.91 g (1 mol) of dimethyl carbonate (having a purity of 99%) were charged to a reaction vessel under a nitrogen purge and mixed at room temperature (23° C.). 4.32 g (0.01 mol) of a 25% strength solution of sodium methoxide in methanol were slowly added into reaction mixture under stirring. No exotherm was observed. After one hour, the temperature was increased to reflux temperature of 77° C. After two hours of stirring at that temperature, the reaction mixture was gradually heated to 90° C., and distillate was removed. At this time the flask was full of white solids, and impossible to stir. This material was diluted with acetone and filtered. The remaining solid compound was analysed by infrared spectroscopy, and no significant amount of ethylene urea was found. Unlike the product of Example 1, this product was only partially soluble in water, and had melting temperature above 150° C.

Example 12

Comparative

A product was prepared by the following procedure:

12.06 g (0.2 mol) of ethylenediamine (having a purity of 99.5%), 20.00 g (0.22 mol) of dimethyl carbonate (having a purity of 99%), and 181.9 g of toluene were charged to a reaction vessel under a nitrogen purge and mixed at room temperature (23° C.). 4.32 g (0.1 mol) of sodium methoxide in methanol was slowly added into reaction mixture under mixing. An exotherm was observed and temperature increase to 58° C. was recorded. After one hour, the temperature was increased to 80° C., and the excess of dimethyl carbonate was refluxed. After further two hours, the distillate was collected. A white precipitate was formed upon cooling of the reaction mixture to room temperature. The reaction mixture was concentrated by distillation under reduced pressure (25 kPa) at 95° C., and the remaining solids were washed with acetone. The product was analysed by infrared spectroscopy and no ethylene urea was found. The product was only partially water soluble, having a melting temperature of 250° C.

Example 13

Comparative

A product was prepared by the following procedure:
120.6 g (2 mol) of ethylenediamine (having a purity of 99.5%), 44.44 g (0.5 mol) of ethylene carbonate (having a purity of 99%) were charged to a reaction vessel under a nitrogen purge and mixed at room temperature (23° C.). No exotherm was observed and temperature was raised to 50° C. After one hour of reaction, the temperature was increased gradually to 120° C. After two further hour of mixing at this temperature, and upon subsequent cooling there was no precipitation. The reaction mixture was concentrated by distillation under reduced pressure (25 kPa) at 95° C. The remaining product was water soluble and partially acetone soluble. The product was analysed by infrared spectroscopy, and no ethylene urea was found.

Example 14

Comparative

A product was prepared by the procedure described in "Applied Catalysis" A: General 341, (2008), pages 133 to 138:
18.0 g (0.3 mol) of ethylenediamine (having a purity of 99.5%), 26.4 g (0.3 mol) of ethylene carbonate (having a purity of 99%), and 118.35 g (2.57 mol) of ethanol and 3.96 g (0.1 mol) of MgO were charged to a reaction vessel under a nitrogen purge and mixed at 40° C. After one hour, the temperature was gradually increased to 95° C. and held for two hours. The solid reaction product was separated by hot filtration. The product was analysed by GC/MS, and found to be only a yield of 5% of ethylene urea.

Example 15

Comparative

A product was prepared by the procedure as described in Fischer, Koch, Ann. 232 (1886) 227:
60.3 g (1 mol) of ethylenediamine (having a purity of 99.5%) and 119.19 g (1 mol) of diethyl carbonate (having a purity of 99%) were charged to a reaction vessel under a nitrogen purge and mixed at room temperature (23° C.). No exotherm was observed. The reaction mixture was held for one hour at 50° C., and then temperature was gradually increased to 120° C., and the reaction mixture was held for one hour at reflux. The solution became cloudy upon distillation in the temperature interval of from 88° C. to 110° C. The temperature was then increased to 120° C. and held for two hours. The solution became clear, and there was no precipitation, and the solution remained clear. The reaction mixture was concentrated by distillation under reduced pressure (25 kPa) at 95° C. The remaining product was analysed by infrared spectroscopy, and no ethylene urea was found. The product of this reaction is not water soluble, but acetone soluble.

Example 16

Comparative

A compound was prepared by the following procedure:
60.3 g (1 mol) of ethylenediamine (having a purity of 99.5%) and 119.19 g (1 mol) of diethyl carbonate (having a purity of 99%) were charged to a reaction vessel under a nitrogen purge and mixed at room temperature. No exotherm was observed. After one hour, 21.6 g (0.1 mol) of a 25% strength solution of sodium methoxide in methanol were slowly added to the reaction mixture under stirring, and an exotherm was observed. The reaction mixture was held for one hour at 50° C., and then the temperature was gradually increased to 90° C., whereupon the reaction mixture was held for one hour at reflux. A white precipitate started to form upon distillation at a temperature from 88° C. to 110° C. The temperature was then increased to 120° C., and held for two hours. A white precipitate containing almost no solvent was formed. The remaining product was not water-soluble and not acetone soluble, with a melting temperature in excess of 200° C. No significant amount of ethylene urea was found.

Example 17

A product according to the invention was prepared by the following procedure:
74.49 g (1.0 mol) of 1,3-diaminopropane having a purity of 99.5%, 45.45 g (0.5 mol) of dimethylcarbonate having a purity of 99%, and 4.5 g (0.05 mol) of a 30% strength solution of sodium methoxide in methanol were charged to a reaction vessel under nitrogen purge, and mixed at room temperature (23° C.). An exotherm was observed, the reaction mixture was kept under cooling at a temperature not exceeding 55° C. The temperature was then slowly increased to 90° C., and held for four hours. A white precipitate was formed that consisted of propylene urea (trimethylene urea, 3,4,5,6-tetrahydro-2(1H)-pyrimidinone) as confirmed by its NMR spectrum.

The invention claimed is:
1. A process for the synthesis of a cyclic alkylene urea comprising
reacting a difunctional aliphatic amine A having two primary amino groups and an aliphatic organic carbonate component C selected from the group consisting of dialkyl carbonates CD and of alkylene carbonates CA, in the presence of a basic catalyst selected from the group consisting of alkoxides of alkali metals of group 1 of the Periodic Table of Elements, and of alkoxides of alkaline earth metals of group 2 of the Periodic Table of Elements, to form the cyclic alkylene urea,
wherein the ratio of the amount of substance n(—NH$_2$) of primary amino groups —NH$_2$ of the difunctional aliphatic amine A to the sum n(C) of the amount of substance n(CD) of carbonate groups of a dialkyl carbonate CD and the amount of substance n(CA) of carbonate groups in an alkylene carbonate CA, is at least 2.2.
2. The process of claim 1 wherein the alkoxides are generated in situ.
3. The process of claim 2 wherein the alkoxides are generated by reacting an alkanol with a compound selected from the group consisting of an alkali hydroxide, an alkali hydride, an alkali amide, an alkaline earth hydroxide, an alkaline earth hydride, and an alkaline earth amide.

4. The process of claim 1, wherein the difunctional aliphatic amine A has two primary amino groups attached to a linear or branched or cyclic aliphatic structure which has from two to twenty carbon atoms.

5. The process of claim 1, wherein the aliphatic organic carbonate component C comprises dialkyl carbonates CD having the structure $R^a$—O—CO—O—$R^b$, where $R^a$ and $R^b$ are the same, or different, and are independently selected from the group consisting of linear and branched alkyl radicals having from one to twelve carbon atoms.

6. The process of claim 5 wherein the dialkyl carbonate CD is selected from the group consisting of dimethyl carbonate, diethyl carbonate, and mixtures of dimethyl carbonate and diethyl carbonate.

7. The process of claim 1, wherein the aliphatic organic carbonate component C comprises alkylene carbonates CA having an alkylene group of from two to six carbon atoms.

8. The process of claim 7 wherein the alkylene carbonate is selected from the group consisting of ethylene carbonate and 1,2-propylene carbonate.

9. The process of claim 1 wherein the amine A is has the structure

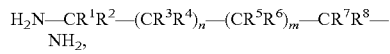

where any of the radicals $R^1$, $R^2$, $R^3$, $R^4$, $R^5$, $R^6$, $R^7$, and $R^8$ may, independently from any other of the said radicals $R^1$, $R^2$, $R^3$, $R^4$, $R^5$, $R^6$, $R^7$, and $R^8$, be H, a halogen atom, a hydroxyl group, an alkyl group having from one to eight carbon atoms and being linear branched or cyclic, an alkenyl group having at least one olefinic unsaturation and from one to eight carbon atoms and being linear branched or cyclic, an alkoxy group having from one to eight carbon atoms and being linear branched or cyclic, or a carboxyl or carboxyl ester group, and where one or more of the radicals $R^3$, $R^4$, $R^5$, and $R^6$ may also be a halogen atom, or a hydroxyl group, and wherein n and m may independently be 0 or 1.

10. The process of claim 1, wherein the basic catalysts are alkali metal alkoxides selected from the group consisting of lithium methoxide, lithium ethoxide, sodium methoxide, sodium ethoxide, potassium methoxide, potassium ethoxide, and mixtures of lithium methoxide, lithium ethoxide, sodium methoxide, sodium ethoxide, potassium methoxide, and potassium ethoxide.

11. The process of claim 1, further comprising the following steps:
charging both the difunctional aliphatic amine A and the carbonate component C to a reaction vessel,
optionally adding a solvent which is selected from the group consisting of aliphatic linear, branched or cyclic alcohols having from one to eighteen carbon atoms, aliphatic glycols having a linear or branched alkylene chain of from two to six carbon atoms, monoalkyl ethers of any of the preceding alcohols where the alkyl groups have from one to four carbon atoms, monoalkyl ethers or dialkyl ethers of any of the preceding glycols where the alkyl groups have independently from one to four carbon atoms, and of alkyl aromatic compounds, and of mixtures of two or more of any of these,
holding the mixture at a temperature of from 0° C. to 250° C.,
adding a basic catalyst under stirring,
further holding the reaction mixture at a temperature of from 25° C. to 250° C. during the reaction, and
isolating the cyclic alkylene urea formed.

12. The process of claim 1, further comprising the following steps:
charging both the difunctional amine A and the basic catalyst to a reaction vessel,
optionally adding a solvent which is selected from the group consisting of aliphatic linear, branched or cyclic alcohols having from one to eighteen carbon atoms, aliphatic glycols having a linear or branched alkylene chain of from two to six carbon atoms, monoalkyl ethers of any of the preceding alcohols where the alkyl groups have from one to four carbon atoms, monoalkyl ethers or dialkyl ethers of any of the preceding glycols where the alkyl groups have independently from one to four carbon atoms, and of alkyl aromatic compounds, and of mixtures of two or more of any of these, holding the mixture at a temperature of from 0° C. to 250° C.,
adding the carbonate component C under stirring,
further holding the reaction mixture at a temperature of from 25° C. to 250° C. during the reaction, and
isolating the cyclic alkylene urea formed.

13. The process of claim 1 wherein the difunctional aliphaticamine A is selected from the group consisting of ethylenediamine, 1,2-diaminopropane, 1,3-diaminopropane, 1,4-diaminobutane, 1,3-diaminobutane, 1,2-diaminobutane, and 2,3-diaminobutane.

14. The process of claim 1 wherein the difunctional aliphatic amine A is ethylenediamine, and the reaction product formed is ethyleneurea.

15. The process of claim 1 wherein the difunctional aliphatic amine A is 1,3-propylenediamine, and the reaction product formed is propyleneurea.

16. The process of claim 1 wherein the difunctional aliphatic amine A is 2-hydroxy-1,3-propylenediamine, and the reaction product formed is 5-hxydroxypropyleneurea.

17. The process of claim 1 wherein the difunctional aliphatic amine A is 2-hydroxy-1,4-diaminobutane, and the reaction product formed is 5-hydroxybutyleneurea.

18. The process of claim 1 wherein the difunctional aliphatic amine A is 2,3-dihydroxy-1,4-diaminobutane, and the reaction product formed is 5,6-dihydroxybutyleneurea.

* * * * *